(12) United States Patent
Wakabayashi

(10) Patent No.: US 11,497,841 B2
(45) Date of Patent: Nov. 15, 2022

(54) METHOD OF FORMING BLOOD ACCESS HOLE, BLOOD ACCESS HOLE, AND BLOOD PURIFICATION METHOD

(71) Applicant: Bousei Daiichi Clinic, Shizuoka (JP)

(72) Inventor: Masanori Wakabayashi, Shizuoka (JP)

(73) Assignee: BOUSEI DAIICHI CLINIC, Shizuoka (JP)

( * ) Notice: Subject to any disclaimer, the term of this patent is extended or adjusted under 35 U.S.C. 154(b) by 1245 days.

(21) Appl. No.: 15/958,245

(22) Filed: Apr. 20, 2018

(65) Prior Publication Data

US 2019/0321538 A1 Oct. 24, 2019

(51) Int. Cl.
| | | |
|---|---|---|
| *A61M 1/36* | (2006.01) | |
| *A61B 17/11* | (2006.01) | |
| *A61B 17/06* | (2006.01) | |
| *A61B 17/3201* | (2006.01) | |
| *A61M 25/09* | (2006.01) | |
| *A61B 90/00* | (2016.01) | |
| *A61M 39/02* | (2006.01) | |

(52) U.S. Cl.
CPC ..... *A61M 1/3655* (2013.01); *A61B 17/06166* (2013.01); *A61B 17/11* (2013.01); *A61B 17/3201* (2013.01); *A61M 1/3659* (2014.02); *A61M 25/09* (2013.01); *A61B 2017/1107* (2013.01); *A61B 2090/3937* (2016.02); *A61M 2039/0258* (2013.01); *A61M 2039/0276* (2013.01)

(58) Field of Classification Search
CPC .. A61M 1/3655; A61M 1/3659; A61M 25/09; A61M 2039/0258; A61M 2039/0276; A61B 17/06166; A61B 17/11; A61B 17/3201; A61B 2090/3937; A61B 2017/1107
See application file for complete search history.

(56) References Cited

U.S. PATENT DOCUMENTS

| | | | | |
|---|---|---|---|---|
| 5,954,691 | A | * 9/1999 | Prosl | A61M 39/0247 604/93.01 |
| 2003/0083678 | A1 | * 5/2003 | Herweck | A61M 1/3661 606/153 |
| 2004/0147867 | A1 | * 7/2004 | Blatter | A61M 1/3653 604/6.16 |
| 2006/0047249 | A1 | * 3/2006 | Shubayev | A61M 1/3659 604/175 |
| 2010/0106161 | A1 | * 4/2010 | Tabbara | A61M 39/0247 606/108 |
| 2010/0191166 | A1 | * 7/2010 | Phillips | A61M 39/0208 604/6.16 |

* cited by examiner

*Primary Examiner* — Philip R Wiest
(74) *Attorney, Agent, or Firm* — Wenderoth, Lind & Ponack, LLP

(57) ABSTRACT

A first method of forming a blood access hole includes: cutting a blood vessel; and connecting the cut blood vessel to a skin. A second method of forming a blood access hole includes: forming an opening in a skin; and connecting a blood vessel, at least a part of which is incised, to the opening. A third method of forming a blood access hole includes: connecting a blood vessel, at least a part of which is incised, to a skin, to open a part of an inner wall of the blood vessel to the atmosphere. A blood access hole 1 in which a blood vessel 10 inside a human body is directly connected to the skin 20 of the human body.

18 Claims, 8 Drawing Sheets

[Fig.1]
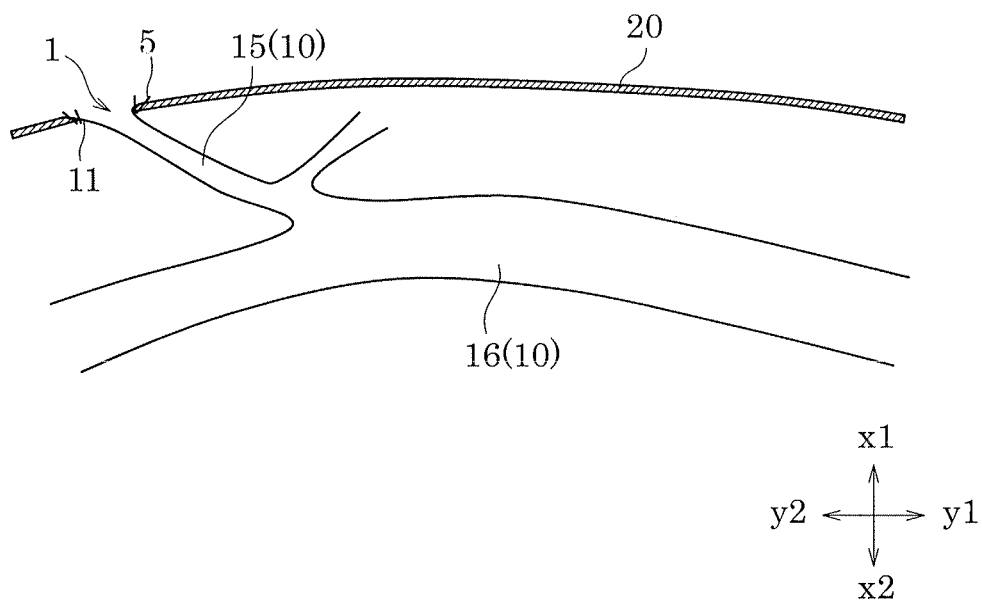
[Fig.2]
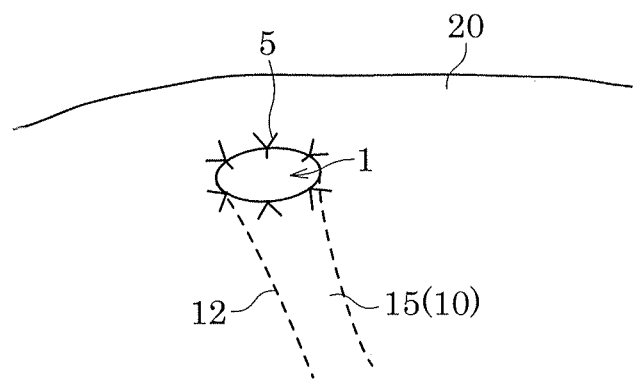

[Fig.3]
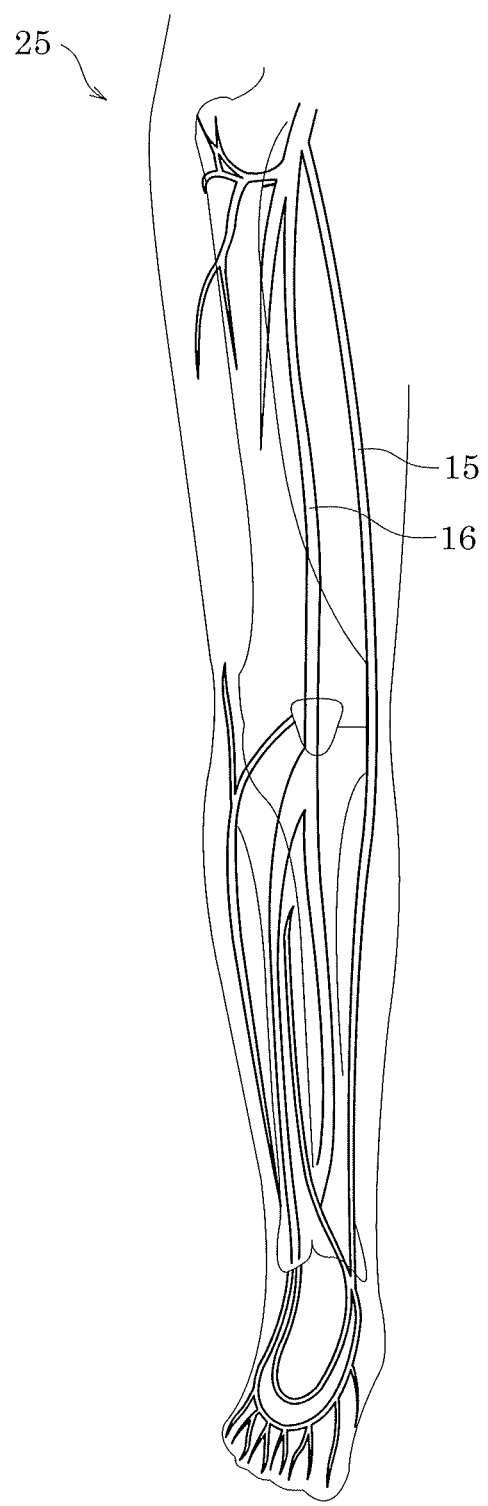

[Fig.4]
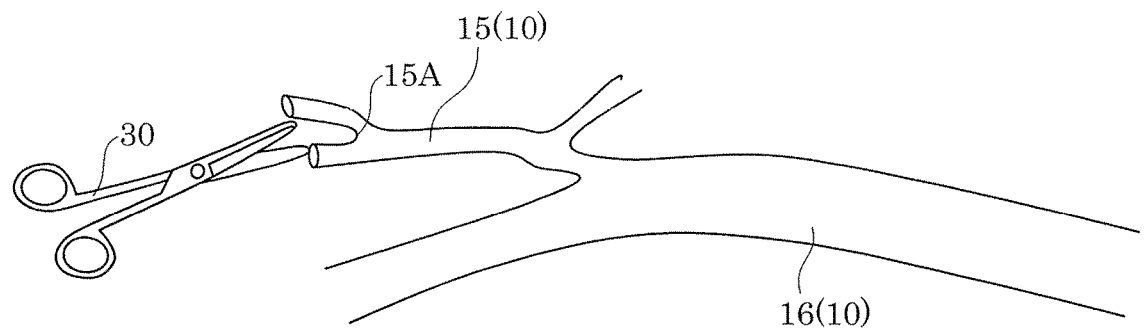
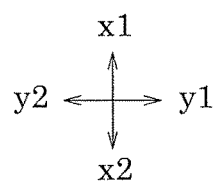
[Fig.5]
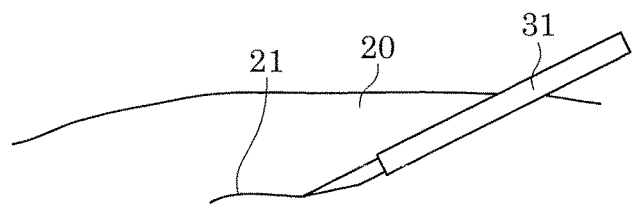
[Fig.6]
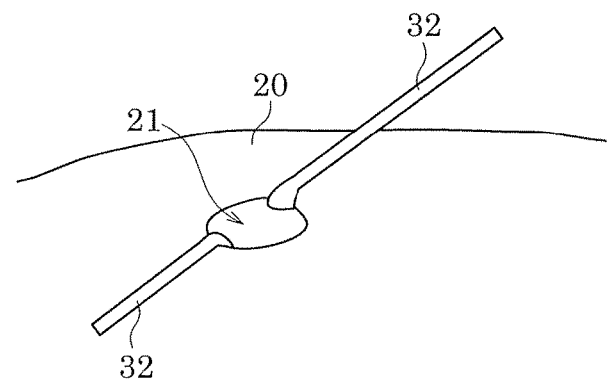

[Fig.7]
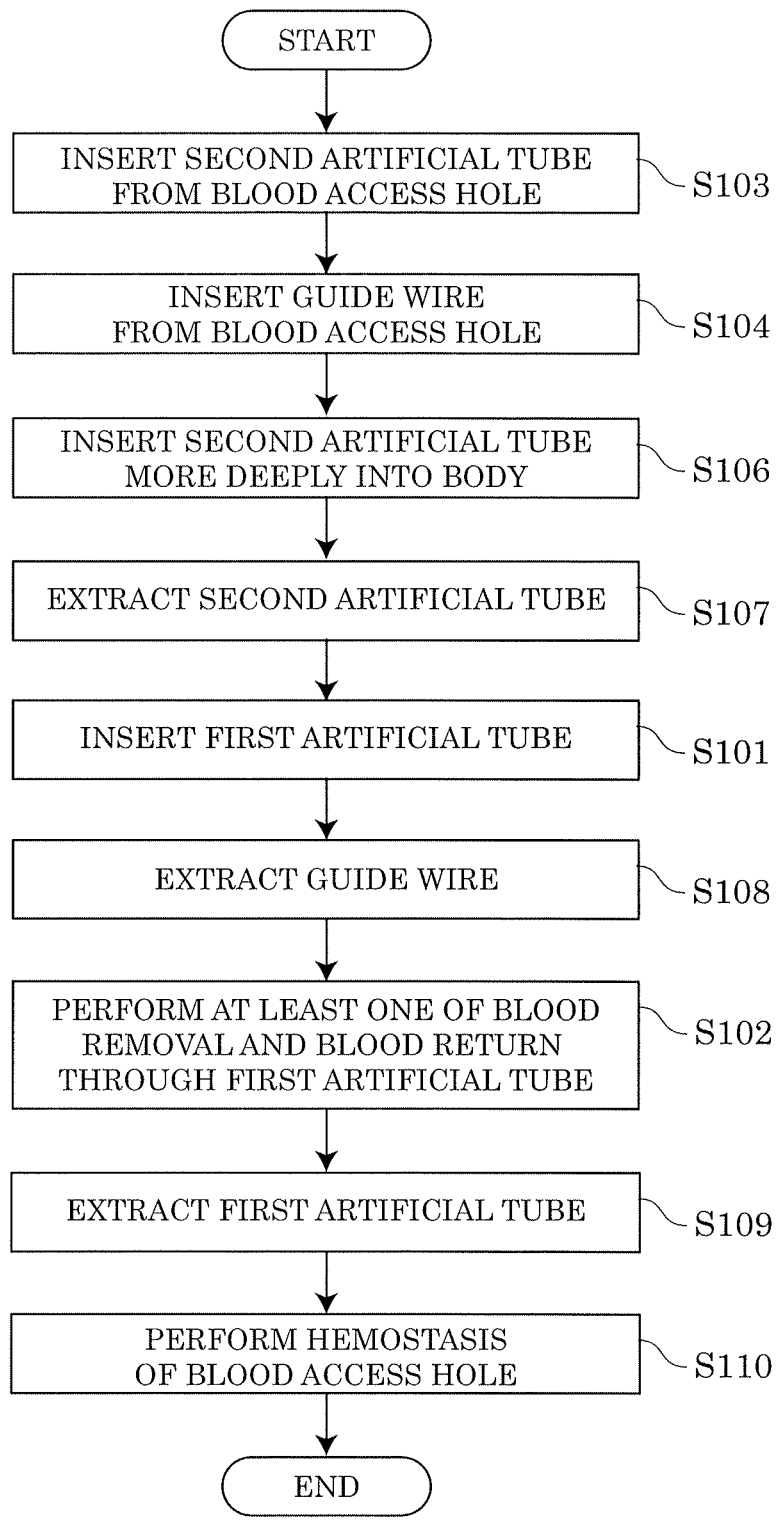

[Fig.8]
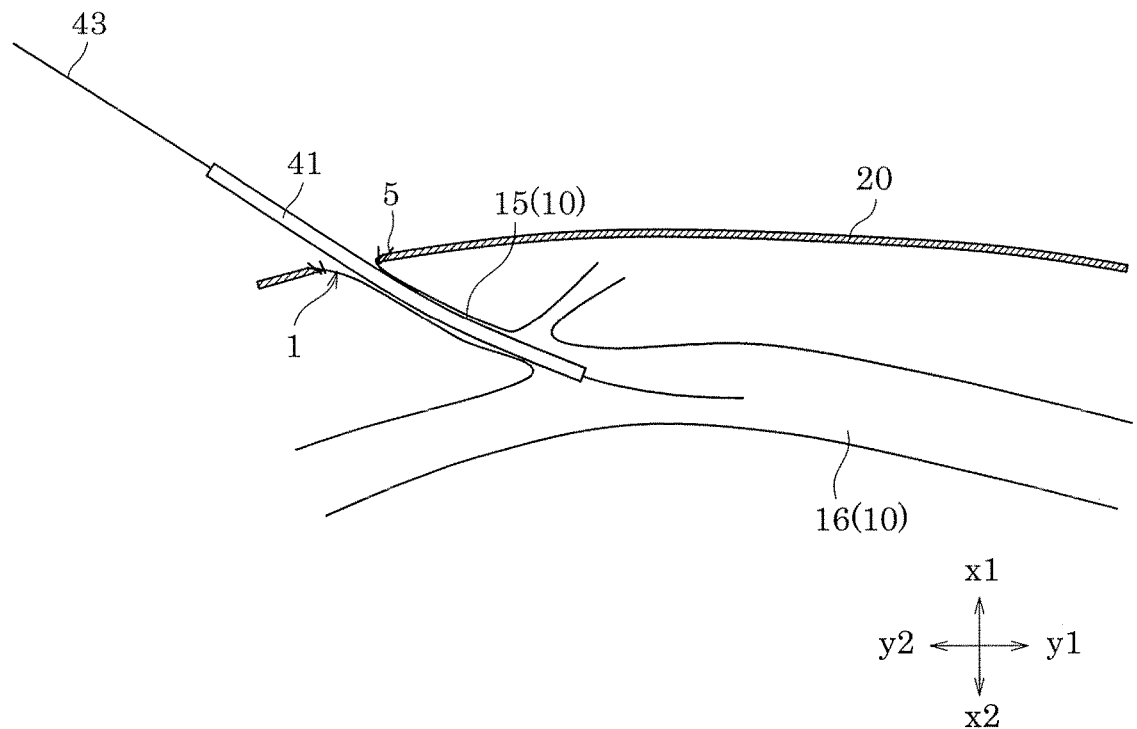
[Fig.9]
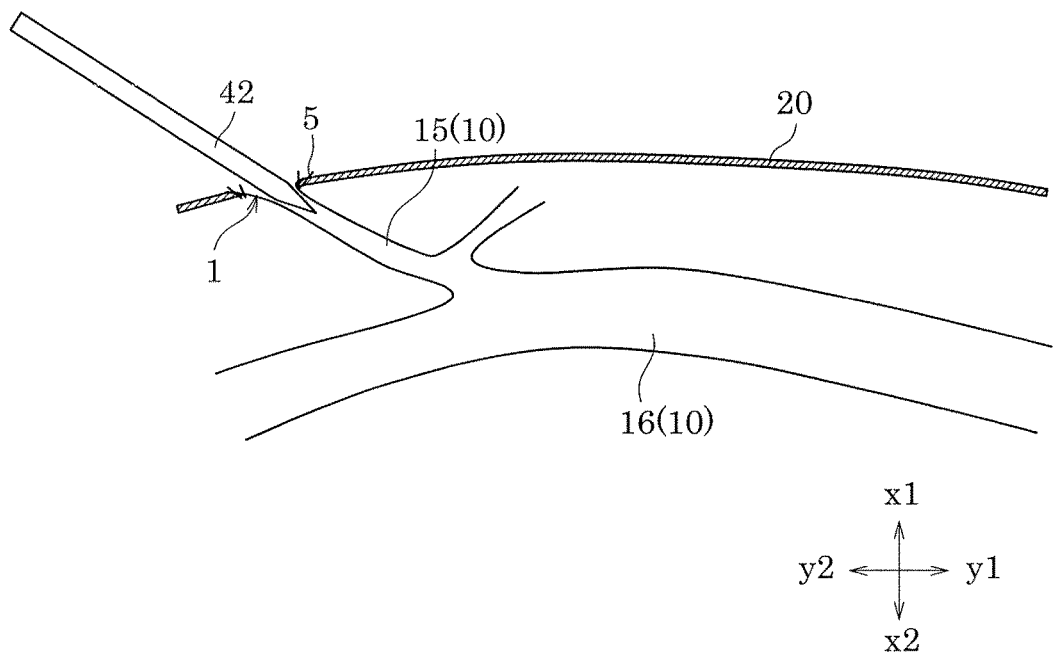

[Fig.10]
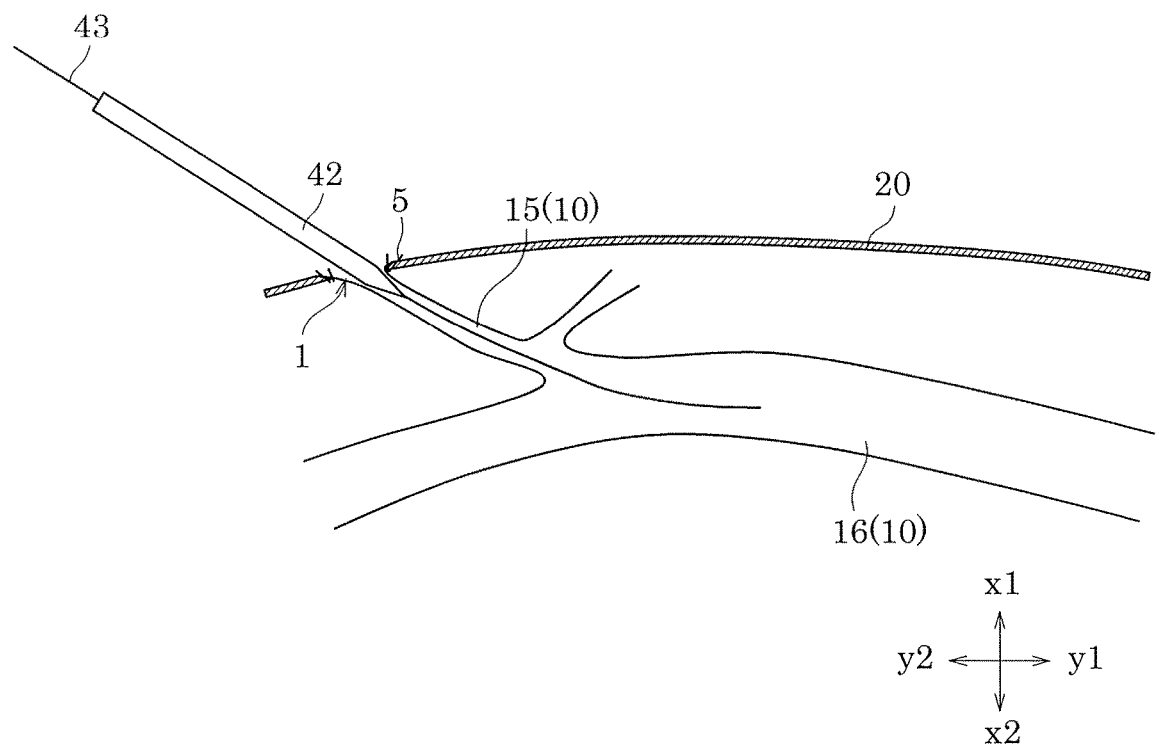

[Fig.11]
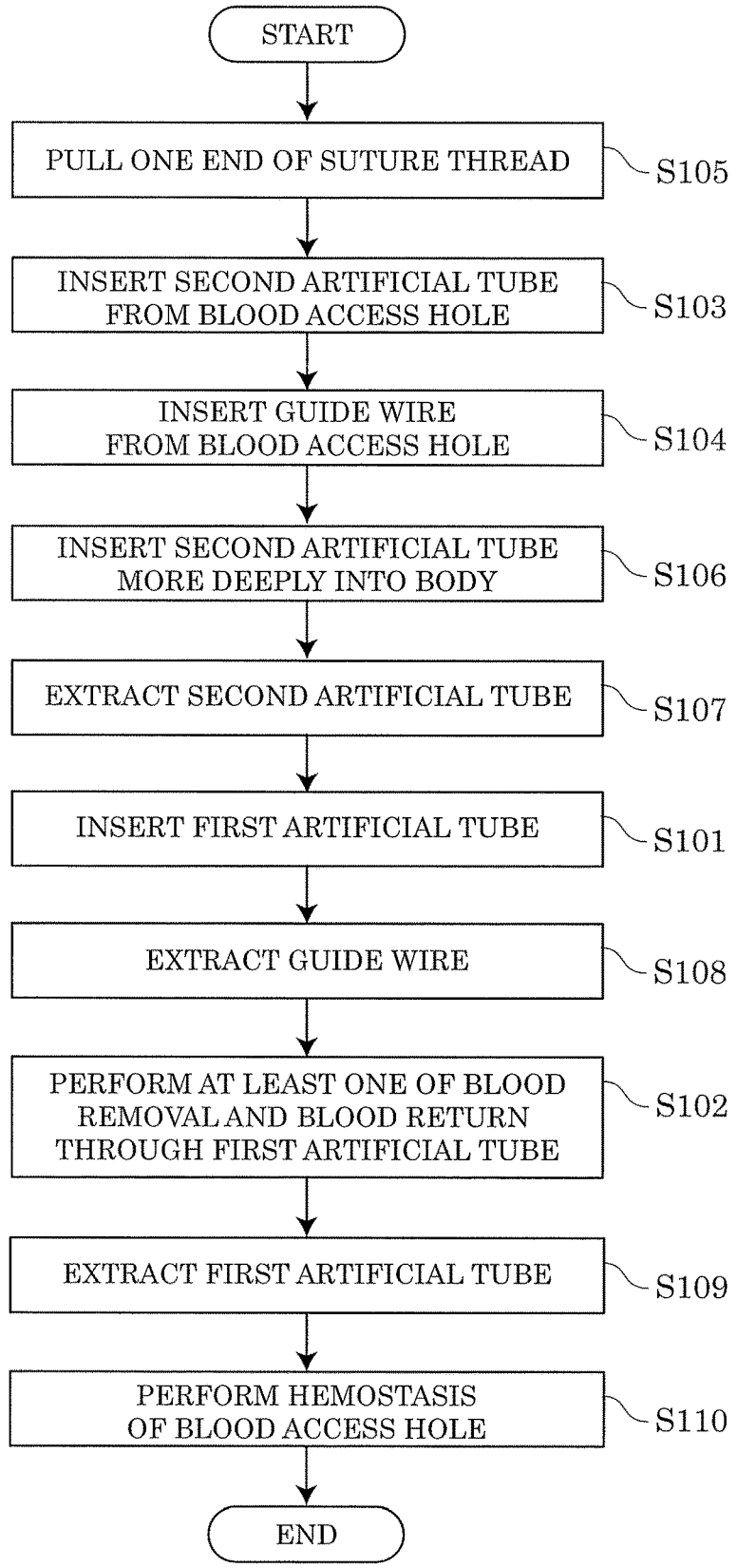

[Fig.12]
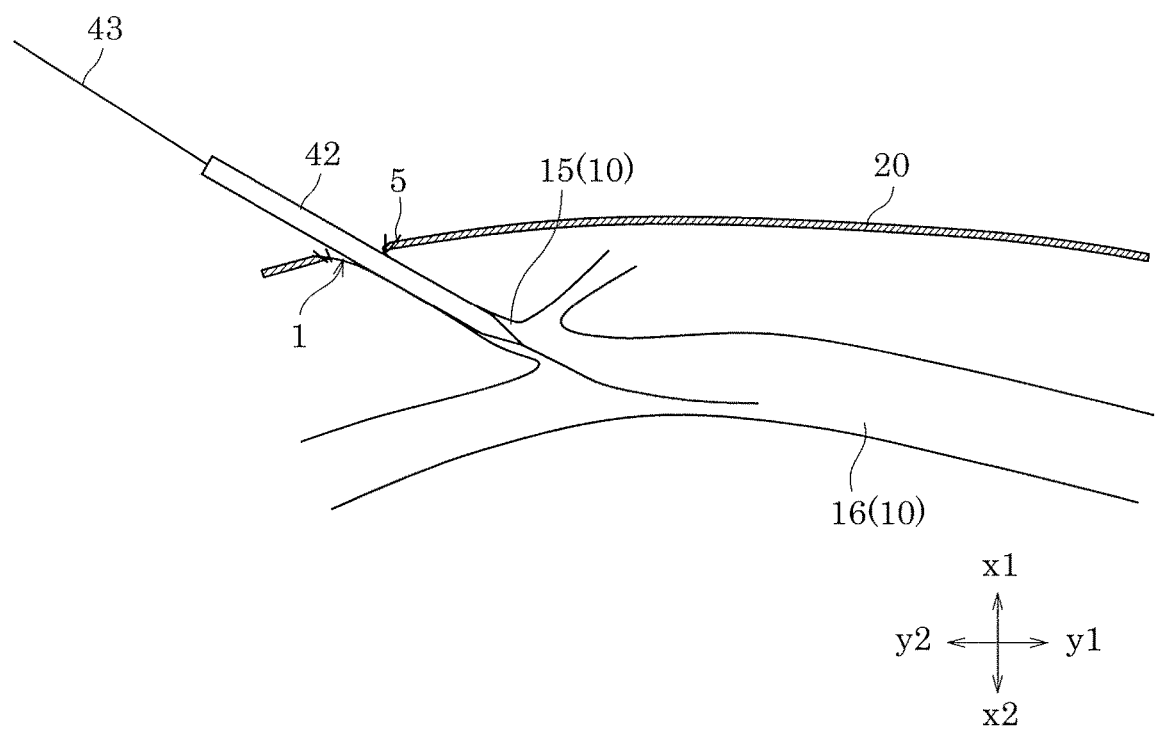

METHOD OF FORMING BLOOD ACCESS HOLE, BLOOD ACCESS HOLE, AND BLOOD PURIFICATION METHOD

TECHNICAL FIELD

The present invention relates to a method of forming a blood access hole, a blood access hole, and a blood purification method used for blood purification such as hemodialysis and plasmapheresis.

BACKGROUND ART

Hemodialysis is usually performed by puncturing a vein with a needle. In order to secure sufficient blood by increasing the blood flow in the vein, an arteriovenous fistula (AVF) that is a connection between an artery to a vein is created in a human body, thereby providing a vascular access (VA). However, there are cases where creation and/or maintenance of such an arteriovenous fistula are difficult depending on conditions of patients, such as deterioration of blood vessels due to aging, occlusion of the arteriovenous fistula, outbreak of infections, and deterioration of cardiac functions. As alternative medical treatments, direct artery puncture and vein puncture via a cuff-type catheter indwelling inside or partly outside a human body, are mainly performed.

Since the artery is present at a position deeper than the skin, the direct artery puncture is a difficult technique, and may cause complications. Meanwhile, in the vein puncture via the cuff-type catheter, since the catheter indwells over a long period, infection or occlusion due to a thrombus resulting from deteriorated blood flow may occur. Since the direct artery puncture and the vein puncture via a cuff-type catheter have various problems, development of alternative medical treatments has been demanded. An object of the present invention is to provide a method of forming a blood access hole, a blood access hole, and a blood purification method for cases where creation of a VA is difficult.

Means for Solving the Problems

A first method of forming a blood access hole of the present invention which is able to achieve the above object includes: cutting a blood vessel; and connecting the cut blood vessel to a skin. Since the first method of forming a blood access hole includes the step of connecting the cut blood vessel to a skin, it is possible to form a blood access hole that allows the outside of a human body and the inside of a blood vessel to communicate with each other.

A second method of forming a blood access hole of the present invention includes: forming an opening in a skin; and connecting a blood vessel, at least a part of which is incised, to the opening. Since the second method of forming a blood access hole includes the step of connecting a blood vessel, at least a part of which is incised, to the opening of the skin, it is possible to form a blood access hole that allows the outside of a human body and the inside of a blood vessel to communicate with each other.

A third method of forming a blood access hole of the present invention includes: connecting a blood vessel, at least a part of which is incised, to a skin, to open a part of an inner wall of the blood vessel to the atmosphere. In the third method of forming a blood access hole, since the blood vessel, at least a part of which is incised is connected to a skin, it is possible to form a blood access hole that allows the outside of a human body and the inside of a blood vessel to communicate with each other.

Accordingly, in blood purification, by using the blood access hole formed by the first to third methods, formation of thrombus, inflammation, narrowing of the vascular lumen resulting therefrom, and infection (hereinafter, it is simply described as "narrowing of a blood vessel lumen and infection".) due to an indwelling artifact are not likely to occur, thereby enabling blood purification even in the case where creation of a VA is difficult.

In the first to third methods of forming a blood access hole, it is preferable that the blood vessel has an outer diameter not less than 2 mm and not greater than 12 mm.

In the first to third methods of forming a blood access hole, it is preferable that the blood vessel is a vein.

In the first to third methods of forming a blood access hole, it is preferable that a marker is provided at a position in a surface area of the skin and within 10 mm from an outer edge of a blood access hole.

In the first to third methods of forming a blood access hole, it is preferable that the blood vessel is connected to the skin by using a colored suture thread.

In the first to third methods of forming a blood access hole, it is preferable that a suture thread used for connection of the blood vessel to the skin extends to the outside of a human body from the surface of the skin by not less than 3 mm.

A blood access hole of the present invention in which a blood vessel inside a human body is directly connected to the skin of the human body. According to the present invention, the outside of a human body and the inside of a blood vessel can be communicated through the blood access hole. When the blood access hole is used for blood purification, it is only necessary to insert and extract a catheter for blood purification (dialysis), that is, it is not necessary to indwell the catheter. Therefore, narrowing of a blood vessel lumen and infection due to an indwelling artifact are not likely to occur. Thus, blood purification can be performed even in the case where creation of a VA is difficult.

In the blood access hole, it is preferable that the blood vessel has an outer diameter not less than 2 mm and not greater than 12 mm.

In the blood access hole, it is preferable that the blood vessel is a vein.

In the blood access hole, it is preferable that a marker is provided at a position in a surface area of the skin and within 10 mm from an outer edge of the blood access hole.

In the blood access hole, it is preferable that the blood vessel is connected to the skin by using a colored suture thread.

In the blood access hole, it is preferable that a suture thread is used for connection of the blood vessel to the skin, and an end of the suture thread extends to the outside of the human body from the surface of the skin by not less than 3 mm.

The present invention provides a blood purification method by using the blood access hole. A first blood purification method of the present invention includes: inserting a first artificial tube into a human body through the blood access hole; and performing at least one of blood removal and blood return through the first artificial tube. In the first blood purification method, since at least one of blood removal and blood return is performed through the blood access hole, it is not necessary to indwell a catheter in a medium to long term period, and therefore, narrowing of a blood vessel lumen and infection due to an indwelling artifact are not likely to occur. Thus, blood purification can be performed even in the case where creation of a VA is difficult.

The blood purification method preferably further includes inserting, into the blood access hole, a second artificial tube that expands an inner diameter of the blood access hole, before the insertion of the first artificial tube.

The blood purification method preferably further includes inserting a guide wire into the human body through the blood access hole, after the insertion of the second artificial tube through the blood access hole and before the insertion of the first artificial tube through the blood access hole.

A second blood purification method of the present invention includes: inserting a first artificial tube into a human body through the blood access hole, and performing at least one of blood removal and blood return through the first artificial tube, the method further includes: inserting, into the blood access hole, a second artificial tube that expands an inner diameter of the blood access hole, before the insertion of the first artificial tube; and pulling an end of the suture thread before the insertion of the second artificial tube. Since the second blood purification method includes the step of pulling an end of the suture thread and the blood access hole can be emphasized, the position of the blood access hole can be easily specified.

In the first and second blood purification methods, it is preferable that the first artificial tube has a blood removal lumen and a blood return lumen.

In the first and second blood purification methods, it is preferable that all the artificial tubes are extracted through the blood access hole each time one blood purification is finished.

According to a method of forming a blood access hole of the present invention, it is possible to form a blood access hole that allows the outside of a human body and the inside of a blood vessel to communicate with each other.

When the blood access hole of the present invention is used for blood purification, it is only necessary to insert and extract a catheter for blood purification (dialysis), that is, it is not necessary to indwell the catheter. Therefore, narrowing of a blood vessel lumen and infection due to an indwelling artifact are not likely to occur. Thus, blood purification can be performed even in the case where creation of a VA is difficult.

Further, according to a first blood purification method of the present invention, it is not necessary to indwell a catheter in a medium to long term period, and therefore, narrowing of a blood vessel lumen and infection due to an indwelling artifact are not likely to occur. Thus, blood purification can be performed even in the case where creation of a VA is difficult. Further, according to a second blood purification method of the present invention, since the blood access hole can be emphasized, the position of the blood access hole can be easily specified.

BRIEF DESCRIPTION OF THE DRAWINGS

FIG. 1 is a schematic diagram showing a blood access hole according to an embodiment of the present invention;

FIG. 2 is a perspective view showing the blood access hole according to the embodiment of the present invention;

FIG. 3 is a schematic diagram showing the position of a greater saphenous vein;

FIG. 4 is a schematic diagram showing step S1-1 of a first method of forming a blood access hole according to the embodiment of the present invention;

FIG. 5 is a schematic diagram showing step S2-1 of a second method of forming a blood access hole according to the embodiment of the present invention;

FIG. 6 is a schematic diagram showing step S2-2 of the second method of forming a blood access hole according to the embodiment of the present invention;

FIG. 7 is a flowchart showing an example of a first blood purification method according to the embodiment of the present invention;

FIG. 8 is a schematic diagram showing step S101 of the first blood purification method according to the embodiment of the present invention;

FIG. 9 is a schematic diagram showing step S103 of the first blood purification method according to the embodiment of the present invention;

FIG. 10 is a schematic diagram showing step S104 of the first blood purification method according to the embodiment of the present invention;

FIG. 11 is a flowchart showing an example of a second blood purification method according to the embodiment of the present invention; and FIG. 12 is a schematic diagram showing step S106 of the first and second blood purification methods according to the embodiment of the present invention.

DESCRIPTION OF EMBODIMENT

Hereinafter, the present invention will be specifically described with reference to the drawings. However, the present invention is not limited to the illustrated examples, and modifications can be made, as appropriate, within the range of the gist described above and below, and such modifications is within the technical scope of the present invention.

1. Blood Access Hole

A blood access hole is an inlet/outlet for blood, which is artificially created between the inside and the outside of a human body. Blood is removed through the blood access hole, and disease agents are separated and eliminated from the blood taken out of the body to purify the blood. The purified blood is returned into the body. The blood access hole is sometimes called a fistula.

Blood purification is widely used as a medical treatment for renal failure, autoimmune diseases, etc. By inserting a catheter into a blood vessel through the blood access hole, blood removal and blood return can be performed. Blood purification methods include hemodialysis and plasmapheresis.

A blood access hole according to an embodiment of the present invention will be described with reference to FIG. 1 to FIG. 3. FIG. 1 and FIG. 2 are a schematic diagram and a perspective view, respectively, showing the blood access hole according to the embodiment of the present invention. FIG. 3 is a schematic diagram showing the position of a greater saphenous vein. In FIG. 1, x1 indicates the side near to the body surface of a patient, x2 indicates the side away from the body surface, and y1 and y2 indicate the head side and the foot side, respectively, in the direction of the height of the patient.

As shown in FIG. 1 and FIG. 2, a blood access hole 1 of the present invention is obtained by directly connecting a blood vessel 10 inside a human body to the skin 20 of the human body. Thus, the outside of the body and the inside of the blood vessel communicate with each other through the blood access hole 1, which allows insertion of a catheter for blood purification through the blood access hole 1.

Conventionally, for cases where creation of a VA is difficult, a cuff-type catheter has sometimes been used, which has an expanded inner diameter at one side in the extending direction thereof. The inner-diameter-expanded part of the catheter is exposed to the outside of the body while a part of the catheter opposite to the inner-diameter-expanded part is inserted into a blood vessel, and blood purification is performed through the catheter. Since the blood purification needs to be repeatedly performed, the cuff-type catheter indwells over a long period. However, the indwelling catheter sometimes causes infection or occlusion due to a thrombus resulting from deteriorated blood flow. Meanwhile, since the blood access hole 1 of the present invention is obtained by directly connecting the blood vessel 10 of the patient to the skin 20 without using an artifact such as a catheter, the outside of the body and the inside of the blood vessel 10 can be communicated with each other through the blood access hole 1. Therefore, when blood purification is performed, it is only necessary to insert and extract a catheter for blood purification (dialysis), that is, it is not necessary to indwell the catheter. Therefore, narrowing of a blood vessel lumen and infection due to an indwelling artifact are not likely to occur. Thus, the blood access hole 1 can be one of options for alternative methods in the case where creation of a VA is difficult.

Preferably, at least a part of the blood vessel 10 is incised to form an incised part 11, and the incised part 11 is connected to the skin 20. The blood vessel 10 may be incised at one end part thereof or at a middle part thereof. The blood vessel 10 may be incised along a direction perpendicular to the extending direction of the blood vessel 10, may be incised obliquely with respect to the extending direction of the blood vessel 10, or may be incised along the extending direction of the blood vessel 10. In any case, the incised part 11 of the blood vessel 10 is preferably connected to the skin 20. By forming the incised part 11 as described above, many connection parts with the skin 20 can be provided, whereby the blood vessel 10 and the skin 20 can be firmly connected to each other.

Preferably, at least a part of the circumference of the blood vessel 10 is connected to the skin 20, and more preferably, the entirety of the circumference of the blood vessel 10 is connected to the skin 20. Thus, the blood vessel 10 is firmly connected to the skin 20, whereby the blood access hole 1 can be ensured, through which insertion and extraction of the catheter for blood purification can be easily performed.

In an area where the blood vessel 10 is connected to the skin 20, the blood vessel 10 is preferably located inward (on the x2 side) of the body relative to the skin 20. In other words, a part of the skin 20 preferably gets into the blood vessel 10 side (the x2 side). By providing the blood access hole 1 as described above, the blood access hole 1 becomes less likely to be closed, which allows blood purification to be repeatedly performed.

The outer diameter of the blood vessel 10 is preferably not less than 2 mm, more preferably not less than 3 mm, and still more preferably not less than 4 mm, but is preferably not greater than 12 mm, more preferably not greater than 10 mm, and still more preferably not greater than 8 mm. The outer diameter of the blood vessel 10 being within the aforementioned range enables blood purification and facilitates connection of the Wood vessel 10 to the skin 20.

Preferably, at least a part, of the blood vessel 10, connected to the blood access hole 1 has the aforementioned outer diameter. Thus, connection of the blood vessel 10 to the skin 20 is facilitated. The blood vessel 10 may have the outer diameter within the aforementioned range throughout the extending direction thereof. Thus, the catheter for blood purification can easily pass through the blood vessel 10.

The blood vessel 10 is preferably a blood vessel other than a capillary vessel, more preferably a vein, still more preferably a superficial vein, and particularly preferably a greater saphenous vein 15. The blood vessel 10 being a vein facilitates blood purification. As shown in FIG. 3, the greater saphenous vein 15 is a superficial vein that joins a femoral vein 16 in a lower limb 25. Since the greater saphenous vein 15 is relatively thick, the blood access hole 1 being formed in the greater saphenous vein 15 allows a sufficient blood removal flow rate to be easily ensured. Since the greater saphenous vein 15 is a superficial vein, the procedure of connecting the blood vessel 10 to the skin 20 is facilitated.

For the purpose of reducing the physical burden on the patient, preferably, one blood access hole 1 is provided for one blood vessel 10, and more preferably, one blood access hole 1 is provided for one patient.

As described later in the section "2. Method of forming blood access hole", the blood vessel 10 and the skin 20 can be connected by suture or by using a stapler for skin, but are preferably sutured with a suture thread 5 as shown in FIG. 1 and FIG. 2. For the purpose of omitting the process of suture removal, the suture thread 5 may be composed of a bioabsorbable polymer material.

Preferably, one blood vessel 10 is connected to the skin 20. Thus, one blood access hole 1 can be provided for one blood vessel 10.

Preferably, a marker is provided at a position in the surface area of the skin 20 and within 10 mm from the outer edge of the blood access hole 1. Such a marker makes visual recognition of the position of the blood access hole 1 easy. More preferably, the marker is provided at a position in the surface area of the skin 20 and within 8 mm from the outer edge of the blood access hole 1, and still more preferably within 5 mm from the outer edge.

The type of marker for the blood access hole 1 is not particularly limited. For example, preferably, the blood vessel 10 is connected to the skin 20 with a colored suture thread 5. Using the colored suture thread 5 makes visual recognition of the position of the blood access hole 1 easy. Preferably, the suture thread 5 is colored with a pigment other than red. More preferably, the color of the pigment is green, blue, violet, or black, for example.

In another embodiment of providing a marker, the suture thread 5 is used for connecting the blood vessel 10 to the skin 20, and one end of the suture thread 5 preferably extends outward from the surface of the skin 20 by not less than 3 mm, more preferably by not less than 4 mm, and still more preferably by not less than 5 mm, but preferably by not greater than 10 mm, and more preferably by not greater than 8 mm.

2. Method of Forming Blood Access Hole

A method of forming a blood access hole will be described. The present invention provides first to third methods of forming a blood access hole. After steps in the respective methods are described, steps to be preferably executed commonly in each method will be described. FIG. 4 is a schematic diagram showing step S1-1 of the first method of forming a blood access hole, FIG. 5 is a schematic diagram showing step S2-1 of the second method of forming a blood access hole, and FIG. 6 is a schematic diagram showing step S2-2 of the second method of forming a blood access hole, according to the embodiment of the present invention.

First Method of Forming Blood Access Hole

First, the blood vessel 10 is cut (step S1-1). The cut blood vessel 10 can be easily connected to the skin 20. FIG. 4 shows an example in which an end part of the greater saphenous vein 15 is cut along the extending direction of the blood vessel 10 with surgical scissors 30. By cutting the greater saphenous vein 15 along a branch part 15A, the opening area of the end part of the greater saphenous vein 15 can be increased. The cutting direction of the blood vessel 10 is not particularly limited. The blood vessel 10 may be cut along the extending direction of the blood vessel 10, or along the direction perpendicular to the extending direction of the blood vessel 10. Alternatively, the blood vessel 10 may be cut obliquely with respect to the extending direction of the blood vessel 10. A surgical knife or surgical scissors can be used for cutting the blood vessel 10.

As shown in FIG. 1 and FIG. 2, the blood vessel 10 having been cut is connected to the skin 20 (step S1-2). In the first method of forming a blood access hole, since the cut blood vessel 10 is connected to the skin 20, the blood access hole 1 can be formed which allows the outside of the body and the inside of the blood vessel 10 to communicate with each other. Therefore, in blood purification, by using the blood access hole 1 formed by the first method of forming a blood access hole, narrowing of a blood vessel lumen and infection due to an indwelling artifact are not likely to occur, thereby enabling blood purification even in the case where creation of a VA is difficult. It is preferable that the circumference of the blood vessel 10 is connected to the skin 20 in a cross-section perpendicular to the extending direction of the blood vessel 10.

Preceding step S1-2, the cut blood vessel 10 may be extended toward the skin 20. Specifically, the blood vessel 10 can be extended along the extending direction, for example. Thus, the blood vessel 10 can be retained in a straight shape, and blood flow is improved, which facilitates blood purification.

Second Method of Forming Blood Access Hole

As shown in FIG. 5, an opening 21 is formed in the skin 20 (step S2-1). The opening 21 can be formed by incising the skin 20. A surgical knife or surgical scissors can be used for forming the opening 21. FIG. 5 shows an example in which the surgical knife 31 is used for forming the opening 21.

The opening 21 is preferably formed at a position corresponding to the blood vessel 10 to be connected. Although a plurality of openings 21 may be formed, it is preferable to form a single opening 21 because dialysis is usually performed using a single catheter. The opening 21 may be formed by incising the skin 20 at a plurality of parts around the position where the blood access hole 1 is desired to be formed. The length of each incised part can be, for example, not less than 5 mm, not less than 1 cm, or not greater than 2 cm.

The size of the opening 21 of the skin 20 can be set as appropriate, depending on the outer diameter of the blood vessel 10 to be connected to the skin 20, or the outer diameter of a catheter to be inserted into the blood vessel 10. For the purpose of reducing the physical burden on the patient, the maximum outer diameter of the opening 21 when being opened with a tool such as a retractor is preferably not less than the outer diameter of the blood vessel 10 to be connected, and can be not less than 2 mm and not greater than 20 mm, for example. Thus, the blood vessel 10 can be easily connected to the skin 20 in step S2-3 described later.

As shown in FIG. 6, preferably, the opening 21 is opened after step S2-1 (step S2-2). By increasing the opening area of the opening 21, the blood vessel 10 can be easily connected to the skin 20. FIG. 6 shows an example in which the opening 21 is opened by hooks 32 being hung on the opening 21. Although not shown in FIG. 6, the opening 21 can be kept open by using a retractor.

Next, the blood vessel 10, at least a part of which is incised, is connected to the opening 21 (step S2-3). In the second method of forming a blood access hole, since the blood vessel 10, at least a part of which is incised, is connected to the opening 21 of the skin 20, the blood access hole 1 that allows the outside of the body and the inside of the blood vessel 10 to communicate with each other can be formed. Accordingly, in blood purification, by using the blood access hole 1 formed by the second method of forming a blood access hole, narrowing of a blood vessel lumen and infection due to an indwelling artifact are not likely to occur, thereby enabling blood purification even in the case where creation of a VA is difficult.

It is sufficient if at least a part of the blood vessel 10 is incised to form a site that is connectable to the skin 20. One end part of the blood vessel 10 may be incised or a middle part of the blood vessel 10 may be incised. The blood vessel 10 may be incised along the direction perpendicular to the extending direction of the blood vessel 10, along a direction oblique to the extending direction of the blood vessel 10, or along the extending direction of the blood vessel 10.

In step S2-3, the circumferential edge of the opening 21 of the skin 20 is preferably connected to the incised part 11 of the blood vessel 10.

Third Method of Forming Blood Access Hole

As shown in FIG. 2, the blood vessel 10, at least a part of which is incised, is connected to the skin 20, whereby a part of a blood vessel inner wall 12 is opened to the atmosphere (step S3-1). In the third method of forming a blood access hole, since the blood vessel 10, at least a part of which is incised, is connected to the skin 20, the blood access hole 1 that allows the outside of the body and the inside of the blood vessel 10 to communicate with each other can be formed. Accordingly, in blood purification, by using the blood access hole 1 formed by the third method of forming a blood access hole, narrowing of a blood vessel lumen and infection due to an indwelling artifact are not likely to occur, thereby enabling blood purification even in the case where creation of a VA is difficult. The blood vessel 10 can be incised in a similar manner as in the second method of forming a blood access hole.

Matters Common to First to Third Methods of Forming Blood Access Hole

Hereinafter, preferable modes of the first to third methods of forming a blood access hole will be described. From the viewpoint of the ease of connection with the skin 20, the outer diameter of the blood vessel 10 to be cut or incised is preferably not less than 2 mm, more preferably not less than 3 mm, and still more preferably not less than 4 mm, but is preferably not greater than 12 mm, more preferably not greater than 10 mm, and still more preferably not greater than 8 mm.

The blood vessel 10 to be cut or incised is preferably a blood vessel other than a capillary vessel, more preferably a vein, still more preferably a superficial vein, and particularly preferably a greater saphenous vein 15.

The method for connecting the blood vessel 10 and the skin 20 is not particularly limited, but it is preferable that at least a part of the circumference of the blood vessel 10 is connected to the skin 20, and it is more preferable that the entirety of the circumference of the blood vessel 10 is connected to the skin 20. Thus, since the blood vessel 10 is firmly connected to the skin 20, the blood access hole 1 can be ensured, which facilitates insertion and extraction of the catheter for blood purification through the blood access hole 1.

The blood vessel 10 and the skin 20 are preferably connected by suture. Thus, the blood vessel 10 and the skin 20 can be reliably connected. As for a suture thread, any of those described in the section "1. Blood access hole" can be used. The suture of the blood vessel 10 and the skin 20 may be interrupted suture or continuous suture. The blood vessel 10 and the skin 20 may be connected by using a stapler.

The suture of the blood vessel 10 and the skin 20 can be performed at predetermined intervals in the circumferential direction of the blood vessel 10. The blood vessel 10 and the skin 20 are preferably connected at not less than four points or at not less than six points, for example. Thus, the blood vessel 10 and the skin 20 are reliably sutured.

A marker is preferably provided during or after the connection of the blood vessel 10 and the skin 20 (step S4-1). The marker makes visual recognition of the position of the blood access hole 1 easy.

The position where the marker is provided is not particularly limited, but, in step S4-1, the marker is preferably provided at a position in the surface area of the skin 20 and within 10 mm from the outer edge of the blood access hole 1. More preferably, the marker is provided at a position in the surface area of the skin 20 and within 8 mm from the outer edge of the blood access hole 1, and still more preferably within 5 mm.

In step S4-1, the blood vessel 10 is preferably connected to the skin 20 by using a colored suture thread. Using the colored suture thread makes visual recognition of the position of the blood access hole 1 easy. As for the colored suture thread, any of those described in the section "1. Blood access hole" can be used.

In step S4-1, in order to emphasize the position of the blood access hole 1, the suture thread used for connection of the blood vessel 10 and the skin 20 is extended to the outside of the body from the surface of the skin 20, preferably by not less than 3 mm, more preferably by not less than 4 mm, and still more preferably by not less than 5 mm, but preferably by not greater than 10 mm, and more preferably by not greater than 8 mm.

3. Blood Purification Method

A method for purifying blood by using the blood access hole described in the section "1. Blood access hole" will be described. First, a first artificial tube and a second artificial tube used in the first and second blood purification methods will be described.

The first artificial tube 41 is a tube having a lumen that allows blood to pass therethrough. The first artificial tube 41 preferably has a blood removal lumen and a blood return lumen. As for the first artificial tube 41, a catheter for hemodialysis may be used, for example. The blood removal lumen and the blood return lumen may have the same inner diameter and the same length in the longitudinal axial direction, or may have different inner diameters and different lengths.

The second artificial tube 42 is used for expanding the inner diameter of the blood access hole. The second artificial tube 42 preferably has a part having an expanded inner diameter along the tube extending direction. The second artificial tube 42 has one end part and the other end part in the extending direction. It is preferable that the outer diameter of the one end part of the second artificial tube 42 is smaller than the inner diameter of the blood vessel 1, and the inner diameter of the other end part extends toward the other end. As for the second artificial tube 42, a dilator may be used, for example.

The length of the second artificial tube 42 in the longitudinal axial direction is preferably shorter than the length of the first artificial tube 41 in the longitudinal axial direction.

First Blood Purification Method

FIG. 7 is a flowchart showing an example of the first blood purification method. As shown in FIG. 8, the first artificial tube 41 is inserted into a human body through the blood access hole 1 (step S101), and at least one of blood removal and blood return is performed through the first artificial tube 41 (step S102). In the first blood purification method, since at least one of blood removal and blood return is performed through the blood access hole 1, it is not necessary to indwell a catheter in a medium to long term period, and therefore, narrowing of a blood vessel lumen and infection due to an indwelling artifact are not likely to occur. Thus, blood purification can be performed even in the case where creation of a VA is difficult. In step S101, as shown in FIG. 8, the first artificial tube 41 is preferably inserted along a guide wire 43 inserted into the human body through the blood access hole 1.

In step S101, the first artificial tube 41 is preferably inserted into a femoral vein 16 via the greater saphenous vein 15 through the blood access hole 1.

In step S102, only blood removal or only blood return may be performed through the first artificial tube 41, or both blood removal and blood return may be performed through the first artificial tube 41.

As shown in FIG. 9, the present invention preferably has step S103 of inserting, into the blood access hole 1, the second artificial tube 42 for expanding the inner diameter of the blood access hole 1, before the insertion of the first artificial tube 41 (step S101). The inner diameter of the blood access hole 1 being expanded allows smooth insertion of the first artificial tube 41.

As shown in FIG. 10, the present invention preferably has step S104 of inserting the guide wire 43 into the body through the blood access hole 1, after step S103 of inserting the second artificial tube 42 through the blood access hole 1 and before step S101 of inserting the first artificial tube 41 through the blood access hole 1. Since the guide wire 43 guides the first artificial tube 41 to the insertion position, the insertion of the first artificial tube 41 can be smoothly performed.

Second Blood Purification Method

FIG. 11 is a flowchart showing an example of the second blood purification method. Steps from S101 to S103 are performed similarly as in the first blood purification method.

Before the insertion of the second artificial tube 42 (step S103), an end of the suture thread 5 is pulled (step S105). Since the second blood purification method includes the step of pulling an end of the suture thread 5, even when the blood access hole 1 is closed, the blood access hole 1 can be opened, thereby facilitating the insertion of the second artificial tube 42.

In step S105, a free end of the suture thread 5, opposite to the end fixed to the skin 20 is preferably pulled. Thus, the blood access hole 1 can be easily opened.

Matters Common to First and Second Blood Purification Methods

As shown in FIG. 12, each of the first and second blood purification methods preferably has step S106 of inserting the second artificial tube 42 more deeply, after step S104 and before step S101. Thus, the blood vessel lumen can be reliably expanded by the second artificial tube 42, before step 101 of inserting the first artificial tube 41 into the body. Therefore, even when there is a difference between the inner diameter of the first artificial tube 41 and the outer diameter of the guide wire 43, the first artificial tube 41 is not likely to be caught by the blood vessel inner wall in step S101, and can be smoothly inserted into the body.

Each of the first and second blood purification methods preferably has step S107 of extracting the second artificial tube 42 from the body, before step S101. It is preferable that step S107 is performed after step S104.

Each of the first and second blood purification methods preferably has step S108 of extracting the guide wire 43 from the body, before step S102. It is preferable that step S108 is performed after step S101.

Each of the first and second blood purification methods preferably has step S109 of extracting the first artificial tube 41 from the body. It is preferable that step 109 is performed after step S102.

Each of the first and second blood purification methods preferably has step S110 of performing hemostasis of the blood access hole 1, after step S102 (more preferably, after step S109). Thus, bleeding from the blood access hole 1 can be suppressed. The hemostasis time is preferably not less than 3 minutes, more preferably not less than 5 minutes, and still more preferably not less than 8 minutes. The hemostasis time may be not more than 15 minutes or not more than 10 minutes.

In the first and second blood purification methods, all the artificial tubes are preferably extracted from the blood access hole 1 each time one blood purification is finished. Thus, a catheter that indwells in a medium to long term period, which has been used in the conventional method, is not necessary, whereby narrowing of a blood vessel lumen and infection due to an indwelling artifact are not likely to occur. The extraction of the artificial tubes from the body is preferably performed within 60 minutes from the insertion of the first artificial tube 41 into the human body through the blood access hole 1, more preferably within 30 minutes, and still more preferably after completion of dialysis, that is, immediately after blood removal or blood return.

EXAMPLES

Formation of Blood Access Hole

According to the method of forming a blood access hole of the present invention, blood access holes were formed in four dialysis patients. Table 1 shows blood access hole formation conditions.

TABLE 1

| | Age (years) | Sex | Time on dialysis (years) | Blood access formation position | Blood access formation time (min) |
|---|---|---|---|---|---|
| Example 1 | 76 | Male | 2 | Left greater saphenous vein | 30 |
| Example 2 | 70 | Female | 0.3 | Right greater saphenous vein | 20 |
| Example 3 | 82 | Male | 2.5 | Right greater saphenous vein | 24 |
| Example 4 | 79 | Female | 1.2 | Left greater saphenous vein | 35 |

In each of Examples 1 to 4, although a little bleeding was recognized, a large amount of bleeding, infection, and occlusion of the blood access hole were not recognized during and after the operation.

Blood Purification

By using the blood access holes formed in Examples 1 to 4, cannulation for blood removal and blood return and cannulation for only blood return were performed by using the first blood purification method of the present invention. Regarding the blood access holes formed in Examples 3 and 4, the cannulations were performed under ultrasonic guide.

Table 2 shows conditions for blood removal and blood return. Regarding the blood access holes formed in Examples 3 and 4, Table 3 shows observation results regarding the average time before indwelling of a blood removal/return needle, and the hemostasis time after extraction of the blood removal/return needle.

TABLE 2

| | Creation of Arteriovenous fistula (AVF) | Total number of days for blood removal and return (days) | Total number of days for blood return only (days) |
|---|---|---|---|
| CExample 1 | Yes | 64 | 40 |
| Example 2 | Yes | 45 | 29 |
| Example 3 | No | 60 | 0 |
| Example 4 | No | 24 | 0 |

TABLE 3

| | Average time from start of procedure to indwelling of blood removal/return needle (sec) | Hemostasis time after extraction of blood removal/return needle (min) |
|---|---|---|
| Example 3 | 92.8 | 5~10 |
| Example 4 | 120 | 5~10 |

Serious complications such as perforation, infection, thrombogenesis, and bleeding due to cannulation were not recognized. Accordingly, it was found that the blood access hole formed by the method of forming a blood access hole of the present invention could be one of options for alternative methods in the case where formation of a VA is difficult.

What is claimed is:

1. A method of forming a blood access hole comprising: cutting a blood vessel; and
connecting the cut blood vessel directly to a skin.

2. The method according to claim 1, wherein the blood vessel has an outer diameter not less than 2 mm and not greater than 12 mm.

3. The method according to claim 1, wherein the blood vessel is a vein.

4. The method according to claim 1, wherein a marker is provided at a position in a surface area of the skin and within 10 mm from an outer edge of a blood access hole.

5. The method according to claim 1, wherein the blood vessel is connected to the skin by using a colored suture thread.

6. The method according to claim 1, wherein a suture thread used for connection of the blood vessel to the skin extends to the outside of a human body from the surface of the skin by not less than 3 mm.

7. A method of communicating the outside of a human body with the inside of a blood vessel, the method comprising:
forming a blood access hole in which a blood vessel inside the human body is cut and directly connected to the skin of the human body.

8. The method according to claim 7, wherein the blood vessel has an outer diameter not less than 2 mm and not greater than 12 mm.

9. The method according to claim 7, wherein the blood vessel is a vein.

10. The method according to claim 7, wherein a marker is provided at a position in a surface area of the skin and within 10 mm from an outer edge of the blood access hole.

11. The method according to claim 10, wherein the blood vessel is connected to the skin by using a colored suture thread.

12. The method according to claim 10, wherein a suture thread is used for connection of the blood vessel to the skin, and an end of the suture thread extends to the outside of the human body from the surface of the skin by not less than 3 mm.

13. A blood purification method comprising:
inserting a first artificial tube into a human body through a blood access hole in which a blood vessel inside the human body is cut and directly connected to the skin of the human body; and
performing at least one of blood removal and blood return through the first artificial tube.

14. The blood purification method according to claim 13, further comprising inserting, into the blood access hole, a second artificial tube that expands an inner diameter of the blood access hole, before the insertion of the first artificial tube.

15. The blood purification method according to claim 14, further comprising inserting a guide wire into the human body through the blood access hole, after the insertion of the second artificial tube through the blood access hole and before the insertion of the first artificial tube through the blood access hole.

16. The blood purification method according to claim 13, wherein the first artificial tube has a blood removal lumen and a blood return lumen.

17. The blood purification method according to claim 13, wherein all the artificial tubes are extracted through the blood access hole each time one blood purification is finished.

18. A blood purification method, comprising:
inserting a first artificial tube into a human body through a blood access hole in which a blood vessel inside the human body is cut and directly connected to the skin of the human body, and performing at least one of blood removal and blood return through the first artificial tube,
inserting, into the blood access hole, a second artificial tube that expands an inner diameter of the blood access hole, before the insertion of the first artificial tube; and
pulling an end of a suture thread before the insertion of the second artificial tube
wherein a marker is provided at a position in a surface area of the skin and within 10 mm from an outer edge of the blood access hole, and
wherein the suture thread is used for connection of the blood vessel to the skin, and the end of the suture thread extends to the outside of the human body from the surface of the skin by not less than 3 mm.

* * * * *